United States Patent
An et al.

(10) Patent No.: US 7,189,724 B2
(45) Date of Patent: Mar. 13, 2007

(54) QUINOXALINE DERIVATIVES HAVING ANTIVIRAL ACTIVITY

(75) Inventors: Haoyun An, Carlsbad, CA (US); Frank Rong, Irvine, CA (US); Jim Wu, Aliso Viejo, CA (US); Clayton Harris, Irvine, CA (US); Sueying Chow, Diamond Bar, CA (US)

(73) Assignee: Valeant Research and Development, Costa Mesa, CA (US)

( * ) Notice: Subject to any disclaimer, the term of this patent is extended or adjusted under 35 U.S.C. 154(b) by 255 days.

(21) Appl. No.: 10/826,439

(22) Filed: Apr. 15, 2004

(65) Prior Publication Data
US 2005/0026923 A1 Feb. 3, 2005

Related U.S. Application Data

(60) Provisional application No. 60/463,257, filed on Apr. 15, 2003.

(51) Int. Cl.
| | | |
|---|---|---|
| A01N 43/58 | (2006.01) | |
| A01N 43/60 | (2006.01) | |
| A61K 31/50 | (2006.01) | |
| A61K 31/495 | (2006.01) | |
| C07D 241/36 | (2006.01) | |

(52) U.S. Cl. ............... 514/249; 514/250; 544/344; 544/347; 544/353

(58) Field of Classification Search ............... None
See application file for complete search history.

(56) References Cited

U.S. PATENT DOCUMENTS

| 3,510,487 | A * | 5/1970 | Bolhofer et al. ............ 260/250 |
|---|---|---|---|
| 3,656,953 | A * | 4/1972 | Schlunke et al. ............ 96/53 |
| 6,103,720 | A * | 8/2000 | Lubisch et al. ............ 514/237.8 |
| 6,482,949 | B1 * | 11/2002 | Sessler et al. ............ 544/343 |
| 6,518,423 | B1 * | 2/2003 | Kaneko et al. ............ 544/34 |
| 2004/0006104 | A1 * | 1/2004 | Bush et al. ............ 514/314 |

OTHER PUBLICATIONS

Spicer et al, "Dimeric Analogs of Non-Cationic Tricyclic Aromatic Carboxamides are a New Class of Cytotoxic Agents" Anti-Cancer Drug Design, vol. 14(3), pp. 281-289 (1999).*
Hawley's Condensed Chemical Dictionary, 12th ed., Richard J. Lewis, Sr. , © 1993 by Van Nostrand Reinhold. p. 594.*
Concise Encyclopedia Chemistry, edited by Drs. Hans-Dieter Jakubke and Hans Jeschkeit, © 1993 by Walter de Gruyter & Co., p. 490.*
McGraw-Hill Dictionary of Chemical Terms, 3rd ed. edited by Sybil P. Parker, © 1984 McGraw-Hill, Inc., p. 200.*
Silk, J.A. "Quinoxaline N-Oxides. V. Further bz-Substituted Derivatives" Journal of the Chemical Society, pp. 2058-2063 (1956).*
Gum and Joullié "Structure vs. Reactivity in Quinoxalinecarboxylic Acids and Esters" Journal of Organic Chemistry, vol. 30(11), pp. 3982-3985 (1965).*
Batulina et al, "N-Oxides of N-phenazinoyl Derivatives of Some α-Amino Acids" Khimiko-Farmatsevticheskii Zhurnal, vol. 4(11), pp. 18-22 (1970). As Abstracted by Caplus.*
Kora et al, "Synthesis and Antimicrobial Activity of Some New 2,3-dichloroquinoxaline-6-sulfonyl Amino Acid Deriviatives" Polish Journal of Chemistry, vol. 62(7-12), pp. 749-756 (1988) As Abstracted by Caplus.*
Sueszer et al, "Preparation and Laboratory Evaluation of Cellulose-Based Ion Permselective Membranes" Desalination, vol. 7(1), pp. 47-50 (1969).*

* cited by examiner

*Primary Examiner*—Zachary C. Tucker
(74) *Attorney, Agent, or Firm*—Brown Raysman Millstein Felder & Steiner LLP; James P. Demers

(57) ABSTRACT

The invention provides substituted quinoxalines having the general formulas

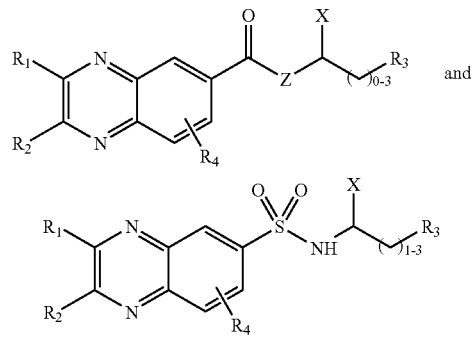

where $R_1$, $R_2$, $R_3$, and $R_4$ are, inter alia, alkyl, aryl, or heteroaryl groups; Z is NH or O; and X is, inter alia, COOH or $CONH_2$. The compounds of the invention have antiviral and immunomodulatory activity and are useful for treating infectious diseases, particularly viral infections.

7 Claims, No Drawings

QUINOXALINE DERIVATIVES HAVING ANTIVIRAL ACTIVITY

RELATED APPLICATIONS

This application claims priority of provisional U.S. application No. 60/463,257, filed Apr. 15, 2003, the contents of which are incorporated by reference herein in their entirety.

FIELD OF THE INVENTION

The field of the invention is pharmaceutical compositions and methods, and especially as they relate to compositions and methods for the treatment of viral diseases.

BACKGROUND OF THE INVENTION

Hepatitis C virus (HCV) infection presents a significant worldwide health problem that affects approximately 170 million people, with about 30,000 new cases in the United States each year. HCV is not easily cleared by the host's immunological defenses, and as many as 85% of the people infected with HCV become chronically infected, often resulting in chronic liver disease, including cirrhosis and hepatocellular carcinoma (Hoofnagle, J. H. 1997, *Hepatology* 26: 15S–20S). Chronic hepatitis C is the leading cause of chronic liver disease, the leading indication for liver transplantation in the United States, and The Centers for Disease Control and Prevention estimates that chronic hepatitis C virus infection is responsible for approximately 10,000 to 12,000 deaths in the United States annually. This number is expected to triple in the next 10 to 20 years without effective intervention.

HCV belongs to the family *Flaviviridae*, genus hepacivirus, which includes three genera of small, enveloped positive-strand RNA viruses. The 9.6 kb genome of HCV consists of a long open reading frame (ORF) flanked by 5' and 3' non-translated regions (NTR's). The polyprotein is cleaved both co- and post-translationally by cellular and viral proteases into at least four structural and six nonstructural (NS) proteins. One of these nonstructural proteins is NS5B, the RNA-dependent RNA polymerase, which plays a central role in viral RNA replication of HCV as well as other viruses of the *Flaviviridae* family.

Unfortunately, the development of effective vaccines for prophylaxis and/or treatment of HCV has been impeded by various virus-specific difficulties, and especially immune evasion. Thus, current treatment of HCV predominantly employs therapeutics that reduce serum HCV levels via monotherapy with (pegylated) interferon-alpha or in combination therapy with the nucleoside analogue ribavirin. While monotherapy results in only 10% sustained virological response (SVS), combination therapy has been shown to improve sustained responses to 54–56% (Michielsen P. et al., 2002, *Acta Gastroenterol Belg* 65(2), 90–94). Clearly, effective antiviral therapies that prevent and alleviate complications suffered by millions of individuals chronically infected with HCV are needed.

Quinoxalines are a well-known class of compounds (O. Hinsberg, J. *Liebigs Ann. Chem* . 237, 327 (1986)), and selected quinoxaline derivatives have been described for use in various therapeutic applications. For example, selected 4-N-aroyl-, arylacyl- and arylsulfonyl-3,4-dihydroquinoxalin-2(1H)-ones were described as anti-inflammatory agents in a series of patent applications by Sumitomo Chem. Co. Ltd. (see e.g., JP 17,137/69, JP 17,136/69, JP 7,008/422, BE 706,623), and 3,4-Dihydroquinoxalin-2(1H)-one-3-carboxamides were described as anti-inflammatory compounds in U.S. Pat. No. 3,654,275. In another example, selected pyridinyl-alkyltetrahydropyrazino[1,2-a]quinoxalinone derivatives were described in U.S. Pat. Nos. 4,203,987 and 4,032,639 as antihypertensive and antisecretory reagents. Furthermore, 4-N-benzenesulfonyl-3,4-dihydroquinoxalin-2(1H)-one-1-alkyl carboxylic acids were reported as aldose reductase inhibitors as described in European Patent Application EP 266,102, and selected quinoxalines were described in U.S. Pat. No. 6,369,057 as therapeutic agents against HIV. However, none of the known quinoxaline derivatives have been demonstrated to exhibit activity against RNA-dependent RNA polymerases, and especially the RNA polymerase NS5B of HCV. The absence of RNA-dependent RNA polymerases in mammals, and the fact that this enzyme appears to be essential to viral replication, would suggest that the NS5B polymerase is an ideal target for anti-HCV therapeutics.

Thus, while numerous therapeutic compounds for treatment of HCV infections are known in the art, all or almost all of them suffer from various disadvantages. Therefore, there is still a need to provide compositions and methods for effective treatment of viral infections, and especially for the effective treatment of HCV infections.

DETAILED DESCRIPTION

The present invention is directed to various classes of quinoxaline derivatives, including their prodrugs and metabolites, and methods of use in the inhibition of viral polymerases, and especially viral RNA-dependent RNA polymerases. The inventors further contemplate numerous compositions and alternative uses for the compounds according to the inventive subject matter, especially as they relate to compounds, compositions and methods for treatment of diseases in humans.

The term "alkyl" as used herein refers to unsaturated hydrocarbon groups in a straight, branched, or cyclic configuration (also referred to as cycloalkyl, see below), and particularly contemplated alkyl groups include lower alkyl groups (i.e., those having six or fewer carbon atoms). Exemplary alkyl groups are methyl, ethyl, propyl, isopropyl, butyl, sec-butyl, tertiary butyl, pentyl, isopentyl, hexyl, isohexyl, etc. The term "alkenyl" as used herein refers to an alkyl as defined above and having at least one double bond. Thus, particularly contemplated alkenyl groups include straight, branched, or cyclic alkenyl groups having two to six carbon atoms (e.g., ethenyl, propenyl, butenyl, pentenyl, etc.). Similarly, the term "alkynyl" as used herein refers to an alkyl or alkenyl as defined above and having at least one triple bond. Especially contemplated alkynyls include straight, branched, or cyclic alkynes having two to six total carbon atoms (e.g., ethynyl, propynyl, butynyl, pentynyl, etc.).

The term "cycloalkyl" as used herein refers to a cyclic alkane (i.e., in which a chain of carbon atoms of a hydrocarbon forms a ring), preferably including three to eight carbon atoms. Thus, exemplary cycloalkanes include cyclopropyl, cyclobutyl, cyclopentyl, cyclohexyl, cycloheptyl, and cyclooctyl. It should further be appreciated that cycloalkyls may also include a double bond. The term "aryl"

as used herein refers to an aromatic carbon atom-containing ring. Thus, contemplated aryl groups include but are not limited to phenyl, naphthyl, and the like. Further contemplated aryl groups may be fused to another aryl group, and are thus termed "fused aryl".

As also used herein, the terms "heterocycle", "cycloheteroalkyl", and "heterocyclic base" are used interchangeably herein and refer to any compound in which a plurality of atoms form a ring via a plurality of covalent bonds, wherein the ring includes at least one atom other than a carbon atom. Particularly contemplated heterocyclic bases include 5- and 6-membered rings with nitrogen, sulfur, or oxygen as the non-carbon atom (e.g., imidazole, pyrrole, triazole, dihydropyrimidine, indole, pyridine, thiazole, tetrazole etc.). Further contemplated heterocycles may be fused (i.e., covalently bound) to another ring or heterocycle, and are thus termed "fused heterocycle" or "fused heterocyclic base" as used herein.

The term "alkoxy" as used herein refers to straight or branched chain alkoxides, wherein the hydrocarbon portion may have any number of carbon atoms (and may further include a double or triple bond). For example, suitable alkoxy groups include methoxy (MeO—), ethoxy, isopropoxy, etc. Similarly, the term "alkylthio" refers to straight or branched chain alkylsulfides, wherein the hydrocarbon portion may have any number of carbon atoms (and may further include a double or triple bond). For example, contemplated alkylthio groups include methylthio (MeS—), ethylthio, isopropylthio, etc. Likewise, the term "alkylamino" refers to straight or branched alkylamines, wherein the hydrocarbon portion may have any number of carbon atoms (and may further include a double or triple bond). Furthermore, the hydrogen of the alkylamino may be substituted with another alkyl group. Therefore, exemplary alkylamino groups include methylamino, dimethylamino, ethylamino, diethylamino, isopropylamino, t-butylamino, etc. Furthermore, the term "alkylsulfonyl" refers to straight or branched chain alkylsulfones, wherein the hydrocarbon portion may have any number of carbon atoms (and may further include a double or triple bond). For example, contemplated alkylsulfonyl groups include methylsulfonyl (MeS(O)$_2$—), ethylsulfonyl, isopropylsulfonyl, etc.

The term "alkyloxycarbonyl" as used herein refers to straight or branched chain esters of a carboxylic acid (derivative) and may have any number of carbon atoms (and may still further include a double or triple bond). Exemplary alkyloxycarbonyl groups include methyloxycarbonyl (MeOC(O)—), ethyloxycarbonyl, and butyloxycarbonyl.

The term "halogen" as used herein refers to fluorine, chlorine, bromine and iodine.

It should further be recognized that all of the above-defined groups might further be substituted with one or more substituents, which may in turn be substituted as well. For example, where a hydrogen atom in an alkyl is substituted with an amino group, one or both hydrogen atoms in the amino group may be substituted with another group (e.g., alky or alkenyl).

The term "substituted" as used herein refers to a replacement of an atom or chemical group (e.g., H, NH$_2$, or OH) with a functional group, and particularly contemplated functional groups include nucleophilic groups (e.g., —NH$_2$, —OH, —SH, —NC, etc.), electrophilic groups (e.g., C(O)OR, C(X)OH, etc.), polar groups (e.g., —OH), non-polar groups (e.g., aryl, alkyl, alkenyl, alkynyl, etc.), ionic groups (e.g., —NH$_3^+$), halogens (e.g., —F, —Cl), NHCOR, NHCONH$_2$, NHCSNH$_2$, OCH$_2$COOH, OCH$_2$CONH$_2$, OCH$_2$CONHR, OC(Me)$_2$COOH, OC(Me)$_2$CONH$_2$, NHCH$_2$COOH, NHCH$_2$CONH$_2$, NHSO$_2$R, NHSO$_2$CF$_3$, OCH$_2$-heterocycles, PO$_3$H, SO$_3$H, (CH$_2$)$_{1-3}$COOH, CH=CHCOOH, O(CH$_2$)$_{1-4}$COOH, NHCOCH$_2$CH(OH) COOH, CH(COOH)$_2$, CH(PO$_3$H)$_2$, OCH$_2$CH$_2$CH$_2$COOH, NHCHO, and all chemically reasonable combinations thereof. Moreover, the term "substituted" also includes multiple degrees of substitution, and where multiple substituents are disclosed or claimed, one or more of the disclosed or claimed substituent moieties can independently substitute the substituted compound.

Thus, the term "functional group" and "substituent" are used interchangeably herein and refer to groups including nucleophilic groups (e.g., —NH$_2$, —OH, —SH, —NC, —CN etc.), electrophilic groups (e.g., C(O)OR, C(X)OH, C(Halogen)OR, etc.), polar groups (e.g., —OH), non-polar groups (e.g., aryl, alkyl, alkenyl, alkynyl, etc.), ionic groups (e.g., —NH$_3^+$), and halogens, as well as NHCOR, NHCONH$_2$, NHCSNH$_2$, OCH$_2$COOH, OCH$_2$CONH$_2$, OCH$_2$CONHR, OC(Me)$_2$COOH, OC(Me)$_2$CONH$_2$, NHCH$_2$COOH, NHCH$_2$CONH$_2$, NHSO$_2$R, NHSO$_2$CF$_3$, OCH$_2$-heterocycles, PO$_3$H, SO$_3$H, (CH$_2$)$_{1-3}$COOH, CH=CHCOOH, O(CH$_2$)$_{1-4}$COOH, NHCOCH$_2$CH(OH) COOH, CH(COOH)$_2$, CH(PO$_3$H)$_2$, OCH$_2$CH$_2$CH$_2$COOH, NHCHO etc.

COMPOUNDS OF THE INVENTION

In one aspect of the inventive subject matter, contemplated quinoxaline derivatives will generally have a structure according to Formula 1:

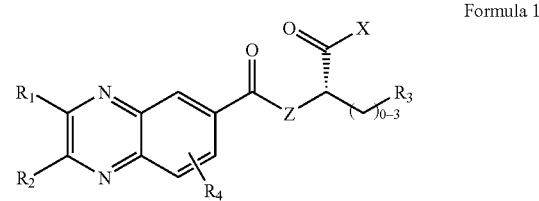

Formula 1 wherein Z is NH or O; X is selected from OH, NH$_2$, OR, NHR, NRR, SH, or SR; R$_1$ and R$_2$ are independently selected from H, substituted or unsubstituted alkyl, alkenyl, alkynyl, aryl, fused aryl, heterocycle or fused heterocycle, and R$_1$ and R$_2$ together with the carbon atoms to which they are attached may form a 5- or 6-membered ring; R$_3$ is substituted or unsubstituted alkyl, alkenyl, alkynyl, aryl, fused aryl, heterocycle or fused heterocycle; and wherein R and R$_4$ are independently H, substituted or unsubstituted alkyl, alkenyl, alkynyl, aryl, fused aryl, heterocycle or fused heterocycle.

In another aspect of the inventive subject matter, contemplated quinoxaline derivatives will generally have a structure according to Formula 2:

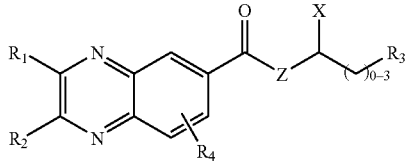

Formula 2 wherein Z is NH or O; X is $CONH_2$, COOR, CONHR, CONRR, COR, heterocycle, R, $SO_3H$, $PO_3H$, $CH(COOH)_2$, $CH(PO_3H)_2$, tetrazole, or triazole; $R_1$ and $R_2$ are independently selected from H, substituted or unsubstituted alkyl, alkenyl, alkynyl, aryl, fused aryl, heterocycle or fused heterocycle, and $R_1$ and $R_2$ together with the carbon atoms to which they are attached may form a 5- or 6-membered ring; $R_3$ is substituted or unsubstituted alkyl, alkenyl, alkynyl, aryl, fused aryl, heterocycle or fused heterocycle; and wherein R and $R_4$ are independently H, substituted or unsubstituted alkyl, alkenyl, alkynyl, aryl, fused aryl, heterocycle or fused heterocycle.

In a further aspect of the inventive subject matter, contemplated quinoxaline derivatives will generally have a structure according to Formula 3:

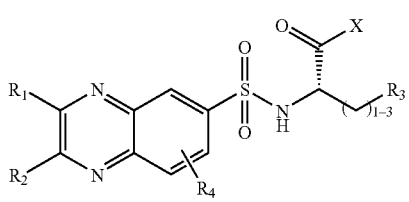

Formula 3 wherein X is $NH_2$, OR, NHR, NRR, heterocycle, or R; $R_1$ and $R_2$ are independently selected from H, substituted or unsubstituted alkyl, alkenyl, alkynyl, aryl, fused aryl, heterocycle or fused heterocycle, and $R_1$ and $R_2$ together with the carbon atoms to which they are attached may form a 5- or 6-membered ring; $R_3$ is substituted or unsubstituted alkyl, alkenyl, alkynyl, aryl, fused aryl, heterocycle or fused heterocycle; and wherein R and R4 are independently H, substituted or unsubstituted alkyl, alkenyl, alkynyl, aryl, fused aryl, heterocycle or fused heterocycle.

In yet another aspect of the inventive subject matter, contemplated quinoxaline derivatives will generally have a structure according to Formula 4 or Formula 5:

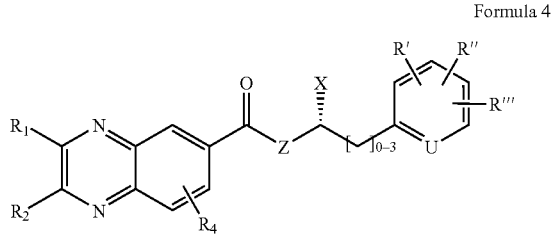

Formula 4

-continued

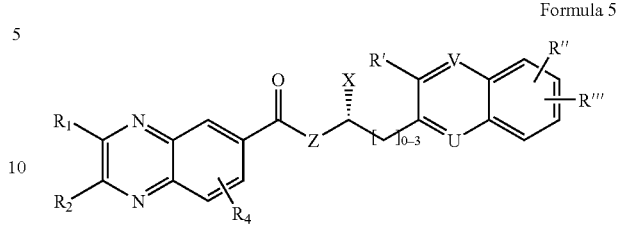

Formula 5 wherein U is selected from CH, CR, COR, CSR, CNHR, CNRR, $CNHCH_2COOH$, $CNHCH_2COOR$, $CNHCH_2CONH_2$, and N; V is N, CH, or CR, or null; Z is NH or O; X is COOH, COOR, $CONH_2$, CONHR, CONRR, $NH_2$, OR, NHR, NRR, SR, or heterocycle; $R_1$ and $R_2$ are independently selected from H. substituted or unsubstituted alkyl, alkenyl, alkynyl, aryl, fused aryl, heterocycle or fused heterocycle, and $R_1$ and $R_2$ together with the carbon atoms to which they are attached may form a 5- or 6-membered ring; R', R'', R''' are independently H, OH, OR, SH, SR, $NH_2$, NHR, NRR, $NO_2$, Cl, F, Br, I, CN, $N_3$, COR, COOH, COOR, $CONH_2$, CONHR, CONRR, C(=NH)NHR, $CH_2CH_2COOH$, $OCH_2COOH$, $NHCONH_2$, NHCHO, $NHSO_2R$, NHCOR, substituted or unsubstituted alkyl, alkenyl, alkynyl, aryl, fused aryl, heterocycle or fused heterocycle; and wherein R and $R_4$ are independently H, substituted or unsubstituted alkyl, alkenyl, alkynyl, aryl, fused aryl, heterocycle or fused heterocycle.

In a still further aspect of the inventive subject matter, contemplated quinoxaline derivatives will generally have a structure according to Formula 6:

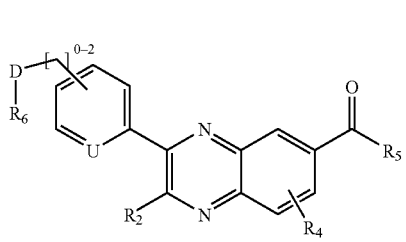

Formula 6 wherein U is selected from CH, CR, COR, CSR, CNHR, CNRR, $CNHCH_2COOH$, $CNHCH_2COOR$, $CNHCH_2CONH_2$, and N; D is O, S, NH, NR, or CRR; $R_5$ is H, OH, SH, OR, SR, $NH_2$, NHR, NRR, O-aryl, or NH-aryl; $R_2$ is H, substituted or unsubstituted alkyl, alkenyl, alkynyl, aryl, fused aryl, heterocycle or fused heterocycle; $R_6$ is H, $CH_2CH_2COOH$, $CH_2COOH$, substituted or unsubstituted alkyl, alkenyl, alkynyl, aryl, fused aryl, heterocycle or fused heterocycle; and wherein R and $R_4$ are independently H, substituted or unsubstituted alkyl, alkenyl, alkynyl, aryl, fused aryl, heterocycle or fused heterocycle.

In another aspect of the inventive subject matter, contemplated quinoxaline derivatives will generally have a structure according to Formula 7:

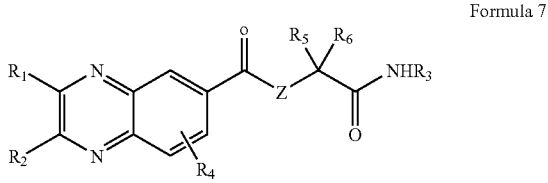

Formula 7 wherein Z is NH or O; $R_1$ and $R_2$ are independently selected from H, substituted or unsubstituted alkyl, alkenyl, alkynyl, aryl, fused aryl, heterocycle or fused heterocycle, and $R_1$ and $R_2$ together with the carbon atoms to which they are attached may form a 5- or 6-membered ring; $R_3$ is substituted or unsubstituted alkyl, alkenyl, alkynyl, aryl, fused aryl, heterocycle, or fused heterocycle, wherein R may further optionally include a COOH group that is covalently coupled to R via zero to three atoms; $R_5$ and $R_6$ are either H, alkyl, or together are connected via an additional 1–4 atoms to form a substituted or unsubstituted cyclic group containing 3–6 atoms; and wherein R and $R_4$ are H, substituted or unsubstituted alkyl, alkenyl, alkynyl, aryl, fused aryl, heterocycle or fused heterocycle.

It should still further be appreciated that where compounds of the invention comprise one or more stereocenters, all diastereomeric and/or enantiomeric forms and all reasonable combinations thereof are expressly contemplated to be within the scope of the invention. For example, although compounds 1 and 3–5 include an asymmetric center that is depicted in only one enantiomeric form, the corresponding opposite enantiomeric forms are also expressly contemplated herein. Similarly, it should be understood that where only one stereoelectronic isomer is depicted, the corresponding other stereoisomeric structures are also contemplated (e.g., keto/enol tautomeric forms, or imine/ketimine tautomeric forms).

Moreover, it should be recognized that prodrugs and metabolites of the compounds according to Formulae 1–9 are contemplated. There are numerous prodrug modifications of pharmacologically active molecules known in the art, and all of such modifications are considered suitable for use herein. However, especially preferred prodrugs include those that deliver compounds of the invention to a target cell (e.g., hepatocyte infected with HCV) or target organ (e.g., liver infected with HCV), wherein the prodrug form may be converted within a cell, organ, or other body compartment in an enzymatic or non-enzymatic manner. Further preferred prodrugs particularly include those in which the prodrug form is less active as compared to the corresponding non-prodrug form. Thus, specifically preferred compounds may include a moiety that increases uptake of the prodrug into a cell, or that increases preferential retention of the compound (which may or may not be in prodrug form) in a cell. Alternatively, the compounds of the invention may be formulated to increase target specificity of the compound (e.g., organ specific liposomes).

With respect to the metabolite, it should be recognized that metabolites of the compounds of the invention might be formed by one or more enzymatic reactions (e.g., via hydrolysis, oxidation, reduction, lyase, or ligase reaction, or even via a polymerase action), or via non-enzymatic reactions (e.g., acid hydrolysis, reduction). For example, a hydrolase or lyase may cleave a portion of compounds of the invention to a more active form. On the other hand, reactions of hydroxylases, ligases, or other enzymes that add chemical groups to the compounds according to the inventive subject matter (to render the compounds more active) are also contemplated herein. Thus, it should be recognized that all metabolites that have a desirable therapeutic effect, and especially an antiviral effect are deemed suitable.

The invention also provides pharmaceutical compositions, comprising a compound of the invention as described herein in, or a pharmaceutically acceptable salt thereof, in combination with a pharmaceutically acceptable carrier. Pharmaceutically acceptable salts are those salts containing one or more non-toxic counterions, including but not limited to sodium, postassium, calcium, and magnesium salts, as well as chloride, bromide, sulfate, acetate, and methanesulfonate salts. Methods of preparing salt forms of pharmaceutical agents are well-known to those of skill in the art.

The invention further provides methods of treating viral diseases, comprising administering a pharmaceutical composition of the invention to a subject in need of such treatment. It is generally contemplated that compounds of the invention will advantageously inhibit a viral polymerase, and especially the RNA dependent RNA polymerase of HCV. Accordingly, such compounds of the invention are expected to be effective in the treatment of HIV-infected individuals. Yet further contemplated uses of the compounds of the invention include treatment of inflammatory diseases, autoimmune diseases, and/or hypertensive disorders.

Thus, in especially preferred aspects of the inventive subject matter, compounds of the invention will have biological activities that include in vitro and in vivo inhibition of RNA-dependent RNA polymerases. It is especially preferred that compounds of the invention may function as a direct inhibitor for an RNA polymerase, and especially for HCV NS5B, but may also serve as a prodrug for delivery to a cell infected with a virus, thereby exhibiting further antiviral effect.

The term "antiviral effect" as used herein refers to both direct and indirect effects, wherein direct antiviral effects include inhibition of a viral polymerase, inhibition of a viral nuclease, inhibition of viral protein processing, inhibition of viral priming activity, inhibition of viral protein assembly, and inhibition of viral entry and/or exit from a cell. Indirect antiviral effects include stimulation of the immune system to increase an immune response, and especially contemplated indirect antiviral effects include modulation of the Th1/Th2 balance (e.g., relative increase of Th1 over Th2, or vice versa), or stimulation of IFN-gamma or IL-12 secretion.

It is particularly contemplated that compounds of the invention are administered to a patient at a concentration effective to reduce viral propagation and replication in a cell infected by the virus. Especially contemplated antiviral activities include at least partial reduction of viral titers of respiratory syncytial virus (RSV), hepatitis B virus (HBV), hepatitis C virus (HCV), herpes simplex type 1 and 2, herpes genitalis, herpes keratitis, herpes encephalitis, herpes zoster, human immunodeficiency virus (HIV), influenza A virus, Hanta virus (hemorrhagic fever), human papilloma virus (HPV), yellow fever virus, and measles virus.

The anti-HCV activity of the quinoxaline derivatives was tested by replicon and BVDV cell-line based assays. The HCV NS5B polymerase activity was tested as described below, and was further tested for its capability of inhibition of replication of the hepatitis C virus in a cell-line based HCV replicon assay as described in V. Lohmann, F. Korner, J.-O. Koch, U. Herian, L. Theilmann, R. Bartenschlager, "Replication of a Subgenomic Hepatitis C virus RNAs in a Hepatoma Cell Line", *Science*, 1999, 285:110.

Pharmaceutical compositions of the invention contain a therapeutically effective amount of a compound of the invention as described herein, in combination with a pharmaceutically acceptable carrier. The term "a therapeutically effective amount" means an amount of the compound sufficient to induce a therapeutic effect, such as antiviral activity. Although the exact amount of active compound used in a pharmaceutical composition of the invention will vary with each compound and according to factors known to those of skill in the art, such as the nature of the carrier and the intended dosing regimen, it is anticipated that the compositions of the invention will contain sufficient active ingredient to provide a dose of about 100 ng/kg to about 50 mg/kg, preferably about 10 µg/kg to about 5 mg/kg in a unit dose. Any conventional dosage form may be used, including but not limited to tablets, lozenges, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including but not limited to immune response modifiers, antivirals, antibiotics, antibodies, proteins, peptides, and oligonucleotides.

Where compounds of the invention are administered in a pharmacological composition, it is contemplated that compounds of the invention can be formulated in admixture with a pharmaceutically acceptable carrier. For example, compounds of the invention can be administered orally as pharmacologically acceptable salts, or intravenously in a physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration. In particular, compounds of the invention may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

In certain pharmaceutical dosage forms, prodrug forms of compounds of the invention may be formed for various purposes, including reduction of toxicity, increasing the organ or target cell specificity, etc. Among various prodrug forms, acylated (e.g. acetylated) derivatives, pyridinecarboxylate esters and various salt forms of the present compounds are preferred. One of ordinary skill in the art will recognize how to readily modify the present compounds to prodrug forms to facilitate delivery of active compounds to a target site within the host organism or patient. One of ordinary skill in the art will also take advantage of favorable pharmacokinetic parameters of the prodrug forms, where applicable, in delivering the present compounds to a targeted site within the host organism or patient to maximize the intended effect of the compound.

Compounds of the invention may be administered alone or in combination with other agents for the treatment of various diseases or conditions. Combination therapies according to the present invention comprise the administration of at least one compound of the present invention or a functional derivative thereof and at least one other pharmaceutically active ingredient. The active ingredient(s) and pharmaceutically active agents may be administered separately or together and when administered separately this may occur simultaneously or separately in any order. The amounts of the active ingredient(s) and pharmaceutically active agent(s) and the relative timings of administration will be selected in order to achieve the desired combined therapeutic effect.

EXAMPLES

1. Synthesis of Compounds

The following experiments are provided to give practitioners guidance on synthesis and use of exemplary compounds of the invention. However, it should be appreciated that various modifications of the below shown experiments may be made without departing from the inventive concepts presented herein.

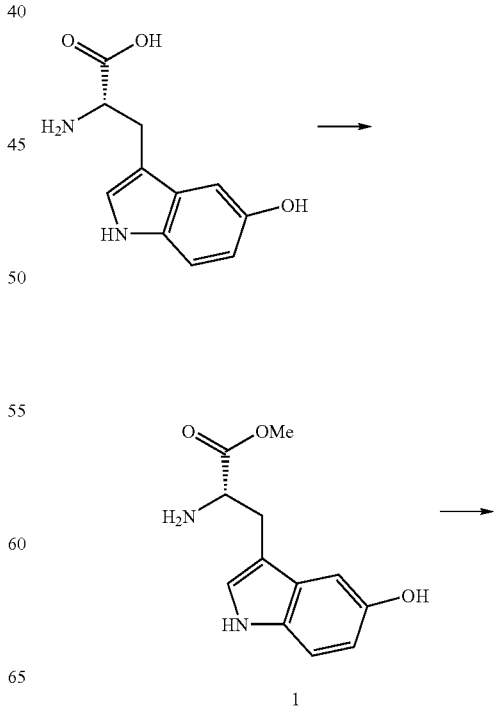

1

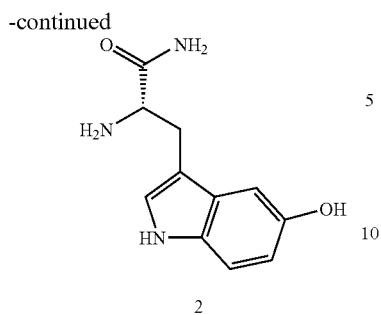

2

Compound 1. To an ice-cooled stirred solution of L-5-hydroxytryptophan methyl ester hydrochloride (2.1 g, 9.53 mmol) in anhydrous methanol (120 ml) was added SOCl$_2$ (6.93 ml, 95.3 mmol) dropwise. The suspension was heated to reflux for 3 hours. After concentrating the mixture to dryness, the resultant residue was taken up in ethyl acetate and washed twice with saturated sodium carbonate and three times with brine. The organic layer was dried over anhydrous Na$_2$SO$_4$ and concentrated to give 910 mg of product 1 as a pale yellow solid in 41% yield, which showed 100% LC-Mass purity; MS(ES) m/z 235 (M+1)$^+$.

Compound 2. To a solution of 1 (717 mg, 3.06 mmol) in 1 ml of methanol was added 10 ml of concentrated NH$_4$OH. The mixture was stirred for 4 hours at room temperature. The reaction was monitored by TLC (CHCl$_3$—MeOH, 2:1) until the starting material 1 dispersed. After removing solvent the residue was dried at 50° C. under vacuum to give 657 mg of 2 as a light brown solid in 98% yield. MS(ES) m/z 219 (M+1)$^+$. The crude product was used in the subsequent step without further purification.

Compound 3. A mixture of 3,4-diaminobenzoic acid (6.8 g, 44.7 mmol), 4-fluorobenzil (10.0 g, 40.6 mmol) and sodium acetate (6.7 g, 81.2 mmol) in 100 ml of acetic acid was boiled for 4 hours under a reflux condenser. The reaction mixture was poured into 500 ml of water while still hot, and the mixture was cooled to room temperature. The precipitate was filtered, and the filtrate was dried under vacuum for 3 hours. The crude product was then dissolved in 400 ml of 3N sodium hydroxide solution, and the product precipitated again by addition of 3N hydrochloric acid solution (400 ml) to pH 3. The compound 3 was obtained in 100% yield as a light brown solid by filtration and dried under vacuum at 50° C. overnight. LC-Mass: 100% purity; TLC Rf(0.85, CHCl$_3$—MeOH, 5:1); MS(ES) m/z 362.9 (M+1)$^+$, 361.5 (M−1)$^−$. $^1$H NMR (DMSO$_{d6}$) δ 7.02–7.12 (m, 4H), 7.38–7.50 (m, 4H), 8.19 (d, 1H, J=5.4 Hz), 8.38 (d, 1H, J=5.4 Hz), 8.78 (s, 1H).

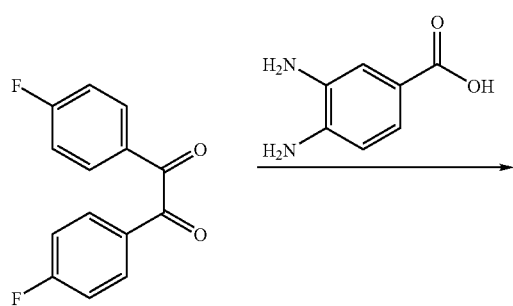

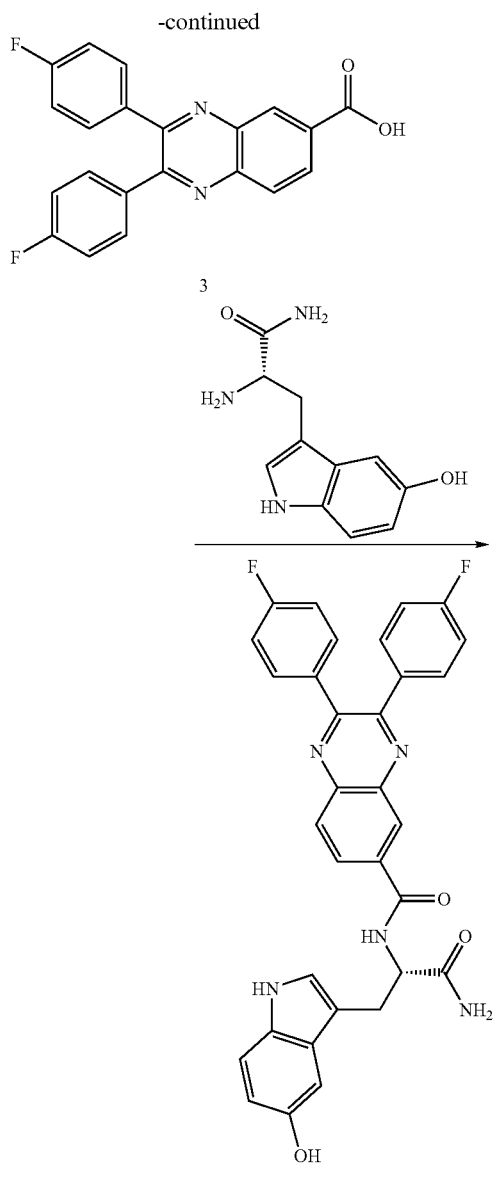

Compound 4. To a solution of 3 (98 mg, 0.27 mmol), O-benzotriazol-1-yl-N,N,N',N'-tetramethyluronium tetrafluoroborate (TBTU) (132 mg, 0.41 mmol) and L-5-hydroxytryptophan amide (90 mg, 0.41 mmol) in 5.0 ml of DMF was added diisopropylethylamine (0.05 ml) dropwise. The reaction mixture was stirred at room temperature for 4 hours and monitored by TLC (CHCl$_3$—MeOH, 5:1). The reaction mixture was quenched by adding 5 ml of water, and the resulting mixture was adjusted to pH 9 by addition of saturated sodium carbonate. The product was extracted with ethyl acetate and washed with brine. The organic layer was dried over anhydrous Na$_2$SO$_4$ and concentrated to dryness. The residue was purified by flash chromatography on a silica gel column using a gradient eluent from 9%–17% methanol in chloroform to give 109 mg (72%) of compound 5 as a pale yellow foam, which showed 96.7% LC-Mass purity. MS(ES) m/z 586 (M+Na)$^+$.

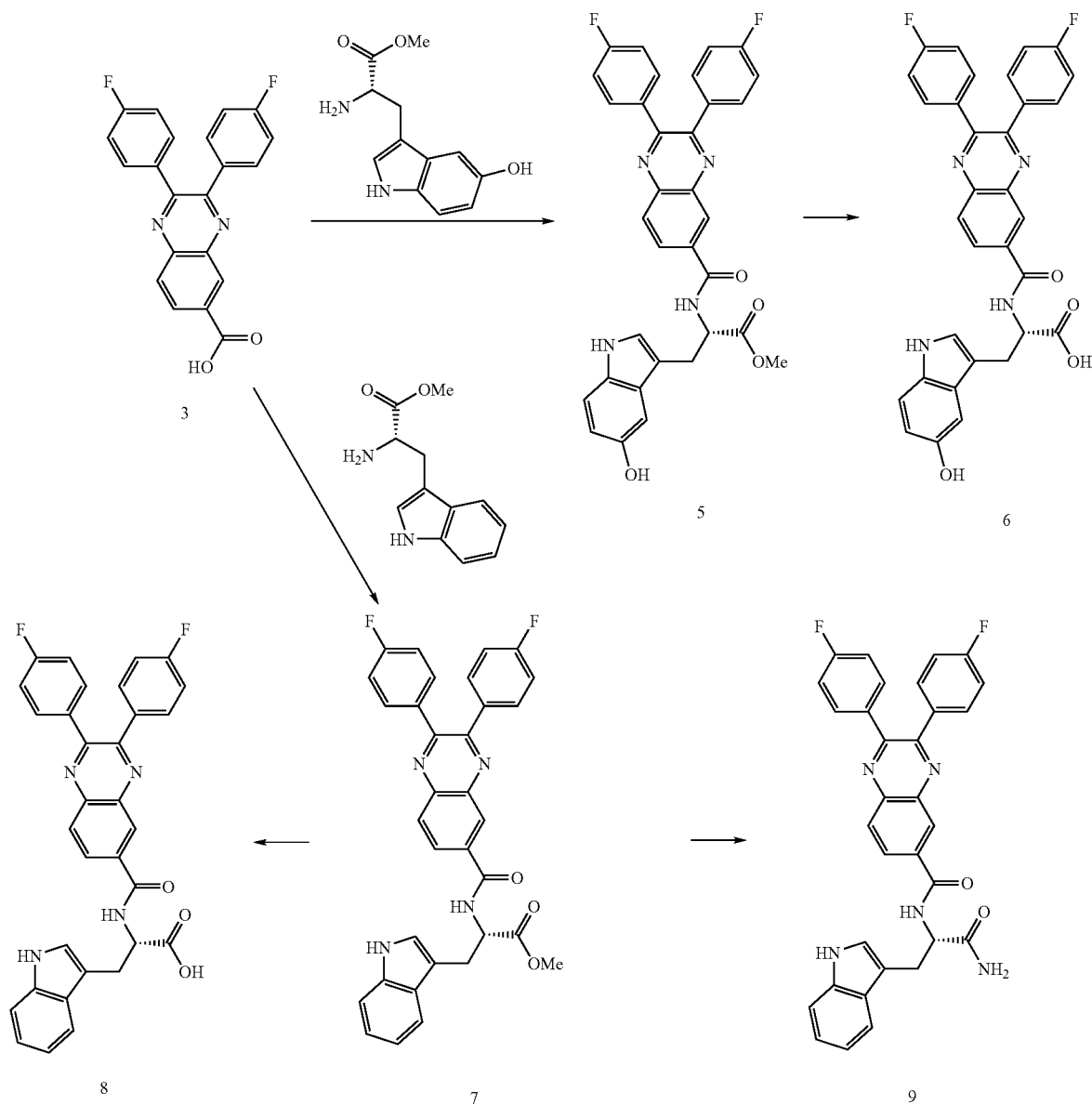

Compound 5. To a solution of 3 (192 mg, 0.53 mmol), O-benzotriazol-1-yl-N,N,N',N'-tetramethyluronium tetrafluoroborate (TBTU) (340 mg, 1.06 mmol) and L-5-hydroxytryptophan methyl ester (174 mg, 0.74 mmol) in 10 ml of DMF was added 0.55 ml of diisopropylethylamine dropwise. The mixture was stirred at room temperature for 16 hours and monitored by TLC ($CHCl_3$—MeOH, 10:1). The reaction mixture was quenched by adding 5 ml of water, and the resultant mixture was adjusted to pH 9 by the addition of saturated sodium carbonate. The mixture was extracted with ethyl acetate and washed with brine. The organic layer was dried over anhydrous $Na_2SO_4$ and concentrated to dryness. The residue was purified to give compound 5 in 51% yield by flash chromatography on a silica gel column using a gradient eluent from 1%–10% methanol in chloroform to give 36.6 mg (51%) of product 5 as a pale yellow foam. MS(ES) m/z 579 (M+H)$^+$.

Compound 6. To an ice-cooled solution of 5 (114 mg, 0.197 mmol) in 5 ml of N,N-dimethylformamide was added 1 ml of 3N sodium hydroxide. The mixture was stirred at room temperature for 2 hours and monitored by TLC ($CHCl_3$—MeOH, 5:1) and API 150EX mass spectrometer. The reaction mixture was quenched by the addition of 3 ml of 1N hydrochloric acid. The mixture was then concentrated to dryness, taken up in EtOAc, and washed twice with water and twice with brine. The organic phase was dried over anhydrous $MgSO_4$ and concentrated to dryness. The residue was purified by flash chromatography on a silica gel column using a gradient eluent from 17%–33% methanol in chloroform. The compound 6 was obtained in 94.6% yield (105 mg) and showed 93.73% HPLC purity. MS(ES) m/z 563 (M−H)$^-$.

Compound 7 was prepared by a similar procedure as described above for compound 5 in 100% yield and showed 98.5% HPLC purity. MS(ES) m/z 563 (M+H)$^+$.

Compound 8 was prepared by saponification as described above for compound 6 in 82.6% yield and showed 97.4% HPLC purity. $^1$H NMR (CD$_3$OD) δ 3.31–3.40 (m, 1H), 3.48–3.55 (m, 1H), 5.00–5.08 (m, 1H), 6.95–7.15 (m, 6H), 7.20 (s, 1H), 7.30 (d, 1H, J=7.8 Hz), 7.50–7.60 (m, 4H), 7.70 (d, 1H, J=7.8 Hz), 8.10–8.20 (m, 2H), 8.48 (s, 1H), 10.30 (s, 1H). MS(ES) m/z 549 (M+H)$^+$, 547 (M−H)$^−$.

Compound 9. To a solution of 7 (116 mg, 0.2 mmol) in 3 ml of dimethylformamide was added 5.0 ml of concentrated ammonium hydroxide. The mixture was stirred at room temperature for 16 hours and monitored by TLC (CHCl$_3$—MeOH, 5:1). The mixture was concentrated to dryness after the starting material dispersed. The residue was purified by flash chromatography on a silica gel column eluting with 10% methanol in chloroform to give 90 mg (83%) of product 9 as a pale yellow foam. The product showed 99.4% HPLC purity. MS(ES) m/z 547 (M−H)$^−$.

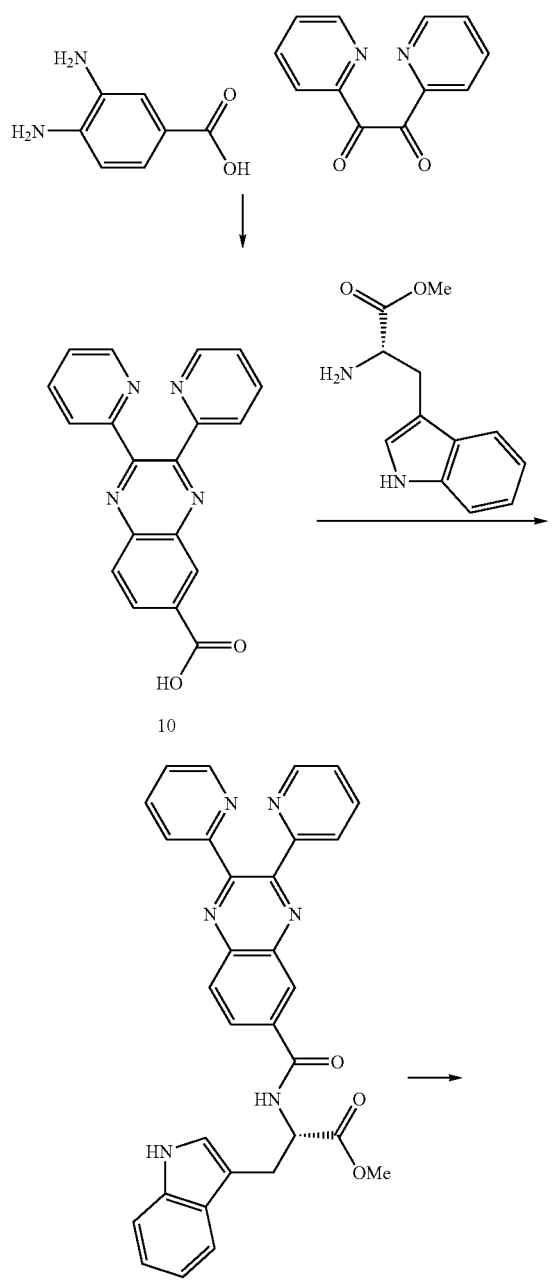

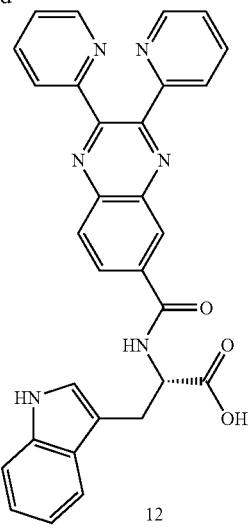

Compound 10 was prepared in 92% yield as a brown solid by the similar procedure as described above for compound 3. MS(ES) m/z 329 (M+H)$^+$.

Compound 11. The carboxylic acid derivative 10 was coupled to L-tryptophan methyl ester hydrochloride in the usual manner as described above for compound 5 to give compound 11 as a pale yellow foam in 83.6% yield. MS(ES) m/z 529 (M+H)$^+$.

Compound 12 was prepared in 69%-isolated yield by saponification of methyl ester 11 and followed by column purification. The product showed 91.99% HPLC purity.

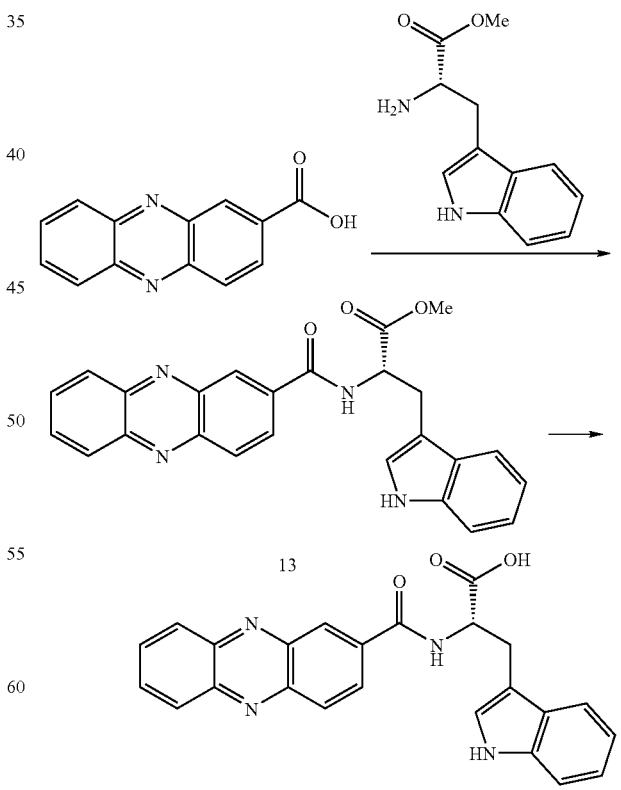

Compound 13 was prepared as a pale yellow foam in 77.4% isolated yield by coupling phenazine-2-carboxylic acid with L-tryptophan methyl ester hydrochloride in the usual manner as described above for compound 5. MS(ES) m/z 425 (M+H)+.

Compound 14 was prepared in 77%-isolated yield by saponification of methyl ester 13 and followed by column purification. The product showed 98% HPLC purity. $^1$H NMR (CD$_3$OD) δ 3.32–3.44 (m, 2H), 3.50–3.62 (m, 1H), 7.01 (t, 1H, J=7.2 Hz), 7.06 (t, 1H, J=7.2 Hz), 7.21 (2, 1H), 7.32 (d, 1H, J=8.1 Hz), 7.65 (d, 1H, J=7.8 Hz), 7.92–8.01 (m, 2H), 8.10–8.30 (m, 4H), 8.57 (s, 1H), 10.33 (s, 1H). MS(ES) m/z 411 (M+H)+, 409 (M−H)−.

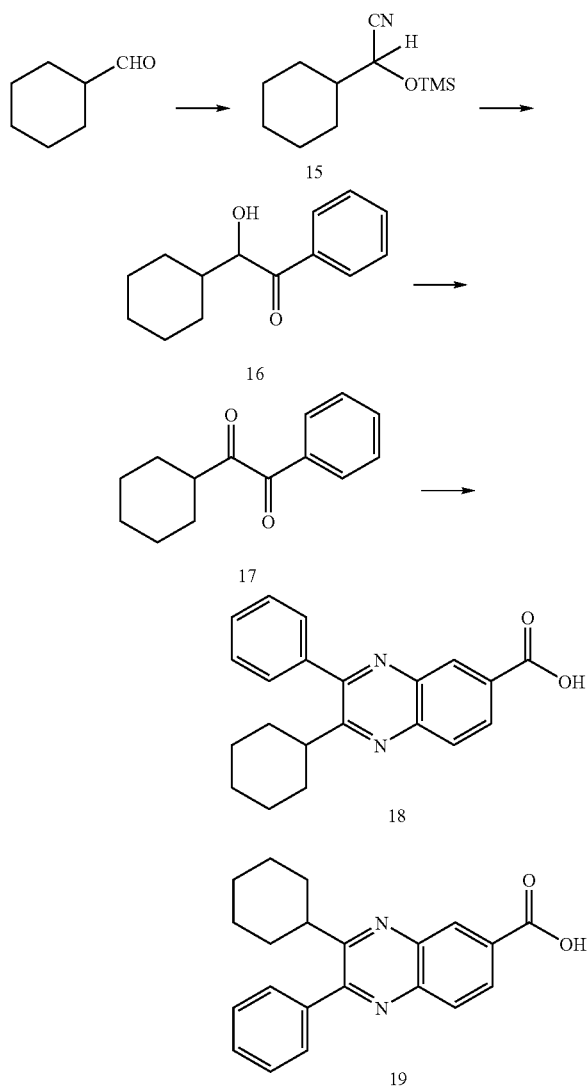

Na$_2$SO$_4$. The solvent was evaporated to dryness. The oily residue was dissolved in 40 ml of anhydrous diethyl ether containing 5 g of MgSO$_4$. The mixture was stirred at room temperature for 3 hours, and then filtered through a pad of silica gel and Na$_2$SO$_4$. The solvent was evaporated, and the residue was dried overnight under vacuum at 40° C. to give 3.71 g (98.5%) of trimethylsilyloxymethylcyclohexane 15 as a yellowish oil.

Compound 16. To an ice-cooled solution of 15 (1.5 g, 7.1 mmol) in 30 ml of diethyl ether was added 3.0 M phenylmagnesium bromide (7.1 ml, 21.29 mmol) dropwise under an argon atmosphere. The reaction mixture was stirred at room temperature for 3 hours and monitored by TLC (Hexanes-EtOAc, 5:1). The cooled reaction mixture was quenched by the addition of 10 ml of water and 15 ml of 10% HCl. The resultant mixture was extracted with AcOEt (40 ml×3). The combined organic layer was washed with brine (30 ml×3) and dried over anhydrous Na$_2$SO$_4$. The solvent was evaporated under vacuum. The oily residue was again dissolved in 20 ml of anhydrous THF and 5 ml of 10% HCl. The mixture was stirred at room temperature for 2 hours. THF was evaporated, and the residue was extracted with AcOEt (50 ml×3). The organic phase was washed with brine (30 ml×3), dried over Na$_2$SO$_4$, and concentrated. The oily residue was purified by flash chromatography on a silica gel column using Hexanes-AcOEt (5:1) as eluent to give 0.39 g of compound 16 in 25% yield.

Compound 17. A solution of 16 (380 mg, 1.74 mmol), copper(II) acetate (31 mg, 0.174 mmol), and ammonium nitrate (174 mg, 2.18 mmol) in 5 ml of 80% (v/v) aqueous acetic acid solution was stirred at room temperature for one hour under an argon atmosphere and then refluxed for 2 hours. The reaction was monitored by TLC (Hexanes-AcOEt, 5:1). The organic solvents were evaporated, and the residue was extracted with diethyl ether (30 ml×3). The combined ether layer was washed with saturated aq. NaHCO$_3$ (20 ml×2) solution and brine (30 ml×3), and dried over anhydrous Na$_2$SO$_4$. The solvent was evaporated, and the residue was purified by flash chromatography on a silica gel column using Hexane-AcOEt (8:1) as eluent to give 211 mg of compound 17 in 56% yield.

Compounds 18 and 19 were prepared in 90% yield by a similar condensation procedure as described above as an isomeric mixture of 18 and 19 in a 3:1 ratio.

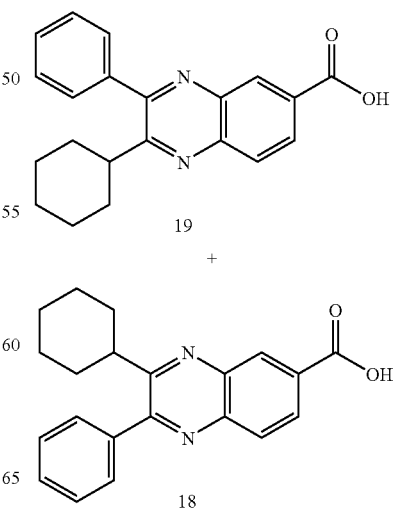

Compound 15. To a solution of cyclohexanecarboxaldehyde (2.16 ml, 17.8 mmol) in 30 ml of anhydrous tetrahydrofuran (THF) was added trimethylsilyl cyanide (2.86 ml, 21.36 mmol) under an argon atmosphere. 0.44 ml of 1.6 M n-BuLi in hexane (0.71 mmol) was added to an ice-cooled reaction mixture under stirring. The reaction mixture was then stirred at room temperature for 2.5 hours, and then quenched by addition of 10 ml of water. After evaporating THF the residue was extracted with diethyl ether (30 ml×3) and the combined organic layer was dried over anhydrous

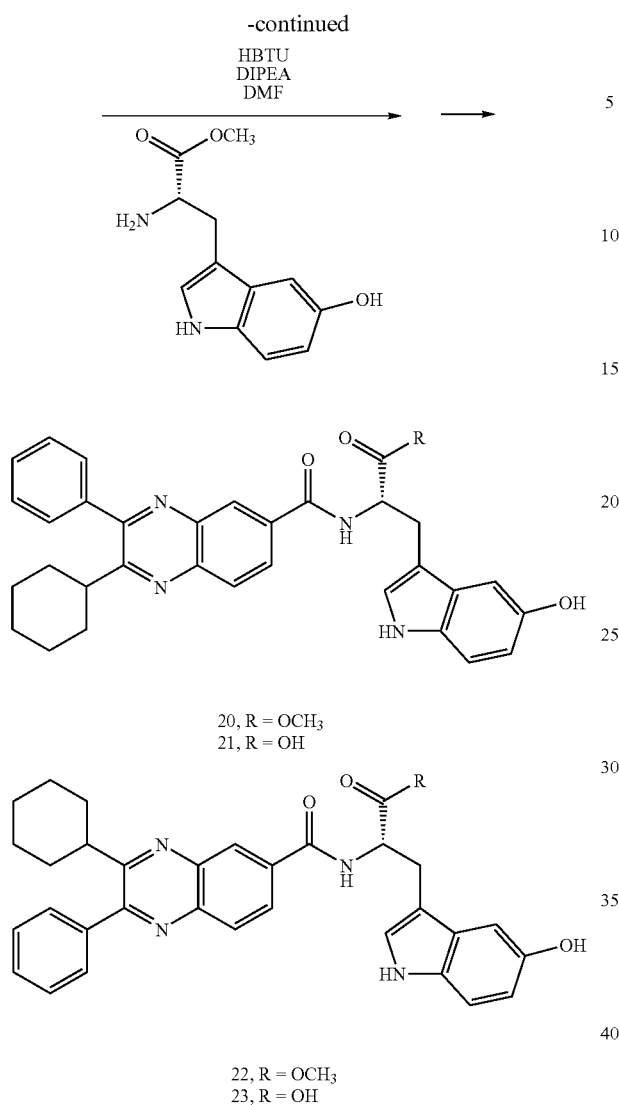
20, R = OCH$_3$
21, R = OH
22, R = OCH$_3$
23, R = OH
Compound 20/22 was prepared as described above for compound 5 as an isomeric mixture in 83% yield. Compound 21/23 was synthesized as described above for compound 6 in 53% yield.
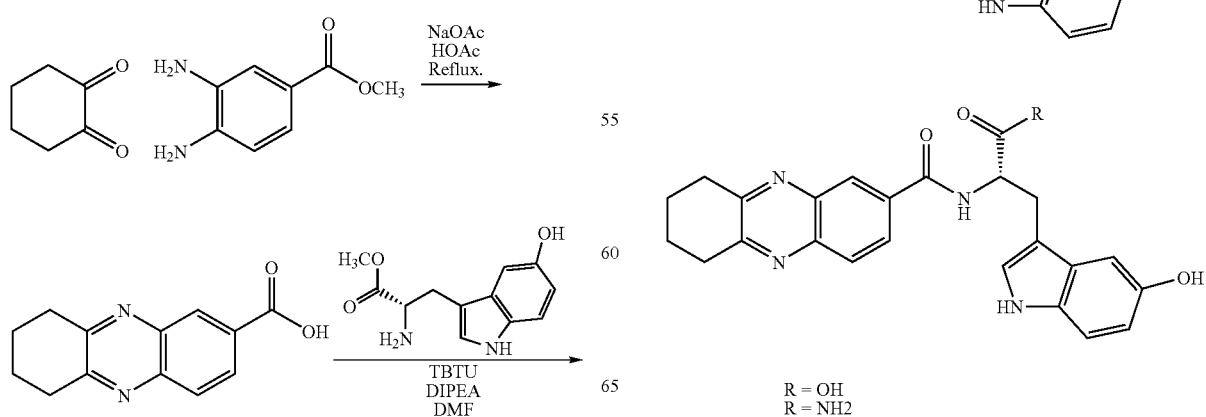
9, R = OH
10, R = NH$_2$
R = OH
R = NH2

Similarly, compounds 24 and 25 may be prepared from the corresponding alpha-hydroxy ester, as shown below:

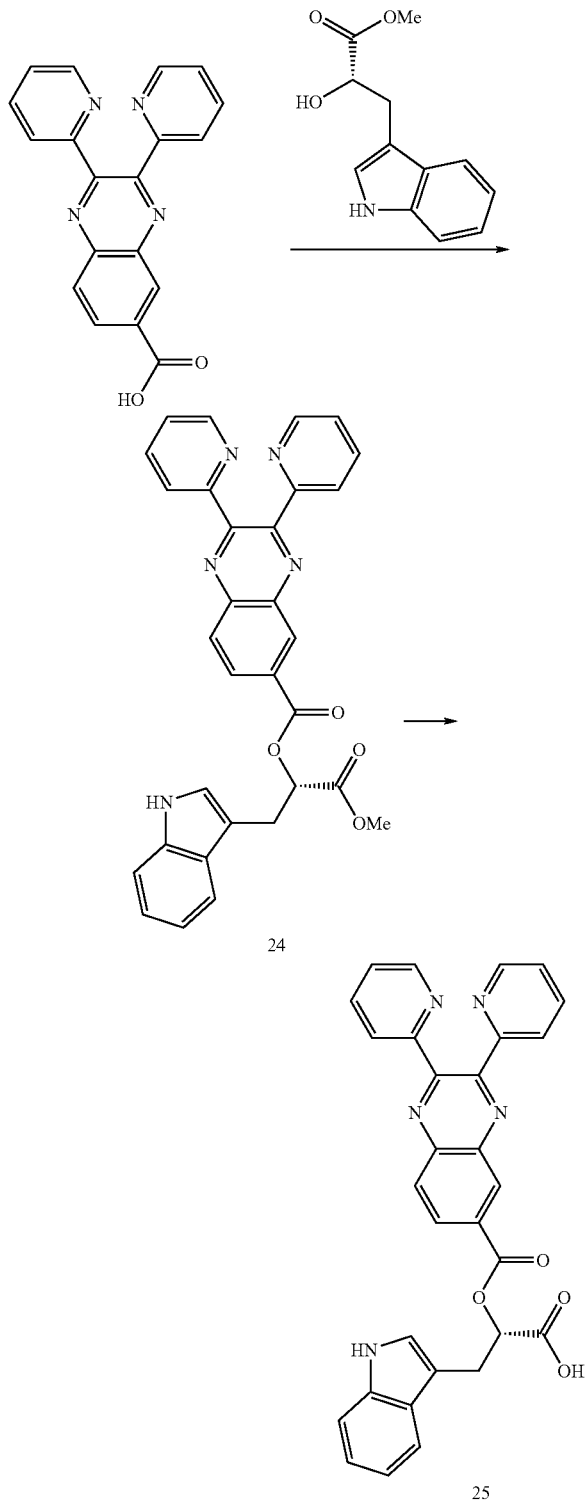

2. Assay of De Novo RNA Synthesis Activity for HCV NS5B Polymerase

HCV NS5B was derived from a cDNA clone encoding HCV-1b CON1 strain, and was expressed and purified from E. coli. Various [α-$^{33}$P]rNTPs (3000 Ci/mmol) were purchased from Perkin Elmer. 3'-Deoxy ribonucleosides, their 5'-triphosphates and dinucleotide primers were from Sigma, TriLink (San Diego, Calif.) or ICN Biochemicals. All other reagents were of the highest grade available from ICN, Sigma, Fisher, or Ambion.

An HCV mini-genome of 2.1-kb contains an entire 5'-UTR (untranslated region), part of NS5B sequence and an entire 3'-UTR was constructed from an internal deletion between two KpnI sites on the HCV replicon plasmid, pFK389/NS3-3'. To generate the in vitro transcribed minigenome RNA, the plasmid DNA was linearized with AseI and ScaI and transcribed in vitro using a MegaScript kit (Ambion, Austin, Tex.). After phenol-chloroform extraction and isopropanol precipitation, the RNA was resuspended in RNase-free water and stored at −80° C. before use. This HCV strain CON1-based template was used for the standard NS5B-catalyzed RNA synthesis assay.

A standard NS5B activity assay was performed at 23C in a total volume of 25 μl. The reaction buffer contained 50 mM Tris, pH 7.0, 10 mM MgCl$_2$, 50 mM NaCl, 5 mM DTT (add fresh) and 0.05 mg/ml BSA. 0.4 μg of the RNA template was incubated with NS5B enzyme (250 nM) before adding a mixture of radiolabeled nucleotide (0.2 μCi) and cold nucleotide cocktail to initiate a reaction. The assay was incubated for 1 hr and terminated by addition of 75 μl of 5% trichloroacetic acid (TCA) and 0.05% pyrophosphate solution. The quenched solution was incubated at room temperature for 10 min to precipitate out polymeric products and subsequently transferred to a 96-well white GF/B filter microplate (Packard Instrument) using a Packard Filtermate Universal Harvester. The filter plate was washed five times by water and one time by ethanol before vacuum drying. 40 μl of liquid scintillation cocktail (Packard MicroSint™) was added to each well. Radioactivity incorporated into the product was counted in a 96-well format using a Packard TopCount. IC$_{50}$ values, defined as the inhibitor concentration to suppress 50% of NS5B activity, were determined by varying the compound concentration. The results in Table 1 are data obtained using the HCV NS5B assays described above.

HCV Replicon Assay. The replicon cells (Huh-7) contain replicating HCV replicon RNA, which was modified in the structural region (replacing the structural region with a neomycin resistance marker). Survival of the replicon cells under G418 selection relies on the replication of HCV RNA and subsequently expression of neomycin phosphoryltransferase. The ability of modified nucleoside libraries and compounds to suppress HCV RNA replication was determined using the QuantiGene™ Assay Kit (Bayer Diagnostics, Tarrytown N.Y.). The assay measures the reduction of HCV RNA molecules in the treated cells. Replicon cells were incubated at 37° C. for 3 days in the presence of nucleoside libraries and compounds before being harvested for detection. The assay protocol was modified based on literature procedure (V. Lohmann, F. Komer, J. O. Koch, U. Herian, L. Theilmann, R. Bartenschlager, *Science*, 1999, 285, 110–113). The HCV subgenomic replicon cell line was provided by Dr. R. Bartenschlager.

Assay for Inhibition of BVDV. The nucleoside libraries and compounds were tested utilizing the modified protocol (V. B. Vassilev, M. S. Collett, R. O. Donis, *J Viol*. 1997, 71, 471–478; S. G. Bagginski, D. C. Pevear, M. Seipel, S. C. C. Sun, C. A. Benetatos, S. K. Chunduru, C. M. Rice, M. S. Collett, *Proc. Natl. Acad. Sci. U.S.A.* 2000, 97, 7981–7986). Bovine viral diarrhea virus (BVDV) (strain NADL) was provided by Dr. Ruben Donis and propagated in MDBK cells (ATCC).

TABLE 1
HCV Replicon and NS5B Inhibitory Activities
| R | X | HCV Replicon (EC50) | HCV NS5B (IC50) |
|---|---|---|---|
| OH | OH | 10–50 μM | <10 μM |
| OCH$_3$ | OH | 10–50 μM | <10 μM |
| NH$_2$ | OH | 10–50 μM | <10 μM |
| OH | H | >50 μM | <10 μM |
| OCH$_3$ | H | 10–50 μM | >50 μM |
| NH$_2$ | H | 10–50 μM | <10 μM |
| R1 | R2 | X | HCV Replicon (IC50) | HCV NS5B (EC50) |
|---|---|---|---|---|
| 4-F-C$_6$H$_4$ | 4-F-C$_6$H$_4$ | OH | >50 μM | <10 μM |
| 4-F-C$_6$H$_4$ | 4-F-C$_6$H$_4$ | OMe | >50 μM | >50 μM |
| 4-Br-C$_6$H$_4$ | 4-Br-C$_6$H$_4$ | OH | 10–50 μM | — |
| C$_6$H$_5$ | C$_6$H$_5$ | OH | >50 μM | <10 μM |
| C$_6$H$_5$ | C$_6$H$_5$ | (N-Me-Trp) | — | 10–50 μM |
| C$_6$H$_5$ | C$_6$H$_5$ | (N-Me-5-OH-Trp) | — | >50 μM |

TABLE 1-continued
HCV Replicon and NS5B Inhibitory Activities
| | | | | |
|---|---|---|---|---|
| 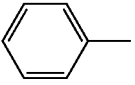 | 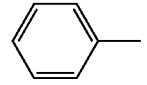 | 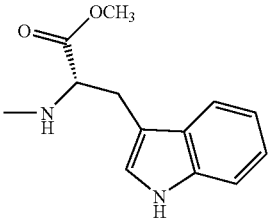 | — | >50 µM |
| 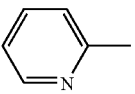 | 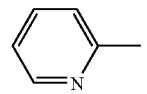 | OH | >50 µM | >50 µM |
| 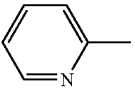 | 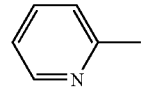 | 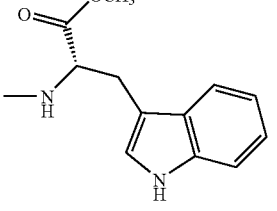 | >50 µM | >50 µM |
| 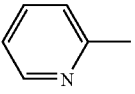 | 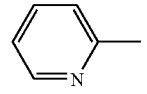 | 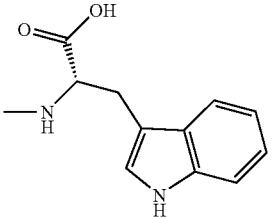 | >50 µM | >50 µM |
| 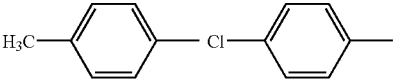 | | OH | 10–50 µM | <10 µM |
| 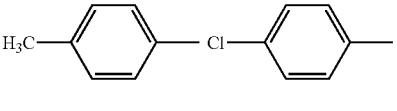 | | 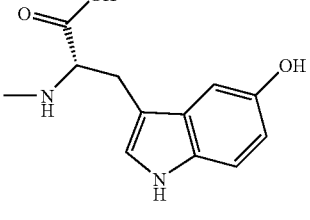 | — | <10 µM |
| 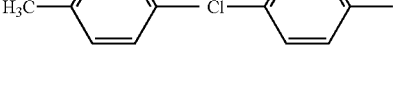 | | 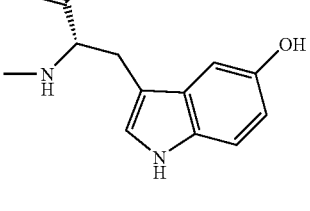 | <10 µMA | — |

TABLE 1-continued

HCV Replicon and NS5B Inhibitory Activities

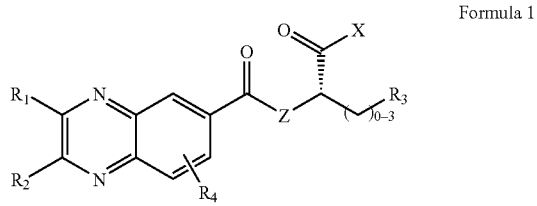

10–50 μM    —

It will be apparent to those skilled in the art that modifications besides those already described are possible without departing from the inventive concepts herein. The inventive subject matter, therefore, is not to be restricted except in the spirit of the specification and claims. Moreover, in interpreting the specification and claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A compound according to Formula 1

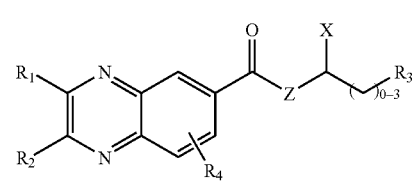

Formula 1 wherein
Z is NH or O;
X is selected from OH, $NH_2$, OR, NHR, NRR, SH, or SR;
$R_1$ and $R_2$ are independently selected from -substituted or unsubstituted alkyl, alkenyl, alkynyl, aryl, fused aryl, heterocycle or fused heterocycle, and $R_1$ and $R_2$ together with the carbon atoms to which they are attached may form a 5- or 6-membered ring;
$R_3$ is substituted or unsubstituted, alkenyl, alkynyl, aryl, fused aryl, heterocycle or fused heterocycle; and
R and $R_4$ are independently H, or substituted or unsubstituted alkyl, alkenyl, alkynyl, aryl, fused aryl, heterocycle or fused heterocycle;
wherein each heterocycle is independently a 5- or 6-membered heterocyclic ring containing at least one atom of S, N, or O,
and wherein substituted groups are substituted with one or more substituents selected from the group consisting of $NH_2$, OH, SH, NC, C(O)OR, aryl, alkyl, alkenyl, alkynyl, F, Cl, Br, NHCOR, $NHCONH_2$, $NHCSNH_2$, $OCH_2COOH$, $OCH_2CONH_2$, $OCH_2CONHR$, $OC(Me)_2COOH$, $OC(Me)_2CONH_2$, $NHCH_2COOH$, $NHCH_2CONH_2$, $NHSO_2R$, $NHSO_2CF_3$, $PO_3H$, $SO_3H$, $(CH_2)_{1-3}COOH$, $CH=CHCOOH$, $O(CH_2)_{1-4}COOH$, $NHCOCH_2CH(OH)COOH$, $CH(COOH)_2$, $CH(PO_3H)_2$, $OCH_2CH_2CH_2COOH$, and NHCHO.

2. A compound according to Formula 2

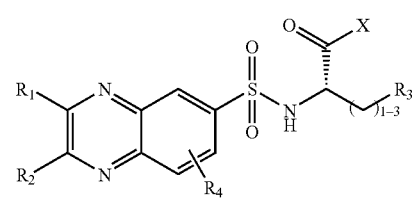

Formula 2 wherein Z is NH or O;
X is $CONH_2$, COOR, CONHR, CONRR, heterocycle, $SO_3H$, $P(O_3H)$, $CH(COOH)_2$, $CH(PO_3H)_2$, tetrazole, or triazole;
$R_1$ and $R_2$ are independently selected from substituted or unsubstituted alkyl, alkenyl, alkynyl, aryl, fused aryl, heterocycle or fused heterocycle, and $R_1$ and $R_2$ together with the carbon atoms to which they are attached may form a 5- or 6-membered ring;
$R_3$ is substituted or unsubstituted, alkenyl, alkynyl, aryl, fused aryl, heterocycle or fused heterocycle; and
R and $R_4$ are independently H, or substituted or unsubstituted alkyl, alkenyl, alkynyl, aryl, fused aryl, heterocycle or fused heterocycle;
wherein each heterocycle is independently a 5- or 6-membered heterocyclic ring containing at least one atom of S, N, or O,
and wherein substituted groups are substituted with one or more substituents selected from the group consisting of $NH_2$, OH, SH, NC, C(O)OR, aryl, alkyl, alkenyl, alkynyl, F, Cl, Br, NHCOR, $NHCONH_2$, $NHCSNH_2$, $OCH_2COOH$, $OCH_2CONH_2$, $OCH_2CONHR$, $OC(Me)_2COOH$, $OC(Me)_2CONH_2$, $NHCH_2COOH$, $NHCH_2CONH_2$, $NHSO_2R$, $NHSO_2CF_3$, $PO_3H$, $SO_3H$, $(CH_2)_{1-3}COOH$, $CH=CHCOOH$, $O(CH_2)_{1-4}COOH$, $NHCOCH_2CH(OH)COOH$, $CH(COOH)_2$, $CH(PO_3H)_2$, $OCH_2CH_2CH_2COOH$, and NHCHO.

3. A compound according to Formula 3,

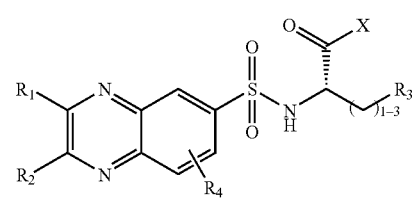

Formula 3 wherein X is $NH_2$, OR, NHR, NRR, heterocycle, or R;
$R_1$ and $R_2$ are independently selected from H, substituted or unsubstituted alkyl, alkenyl, alkynyl, aryl, fused aryl, heterocycle or fused heterocycle, and $R_1$ and $R_2$ together with the carbon atoms to which they are attached may form a 5- or 6-membered ring;

$R_3$ is substituted or unsubstituted alkyl, alkenyl, alkynyl, aryl, fused aryl, heterocycle or fused heterocycle; and R and $R_4$ are independently H, or substituted or unsubstituted alkyl, alkenyl, alkynyl, aryl, fused aryl, heterocycle or fused heterocycle;

wherein each heterocycle is independently a 5- or 6-membered heterocyclic ring containing at least one atom of S, N, or O, and wherein substituted groups are substituted with one or more substituents selected from the group consisting of $NH_2$, OH, SH, NC, C(O)OR, aryl, alkyl, alkenyl, alkynyl, F, Cl, Br, NHCOR, $NHCONH_2$, $NHCSNH_2$, $OCH_2COOH$, $OCH_2CONH_2$, $OCH_2CONHR$, $OC(Me_2)_2COOH$, $OC(Me)_2CONH_2$, $NHCH_2COOH$, $NHCH_2CONH_2$, $NHSO_2R$, $NHSO_2CF_3$, $PO_3H$, $SO_3H$, $(CH_2)_{1-3}COOH$, $CH=CHCOOH$, $O(CH_2)_{1-4}COOH$, $NHCOCH_2CH(OH)COOH$, $CH(COOH)_2$, $CH(PO_3H)_2$, $OCH_2CH_2CH_2COOH$, and NHCHO.

4. A compound according to Formula 4 or Formula 5

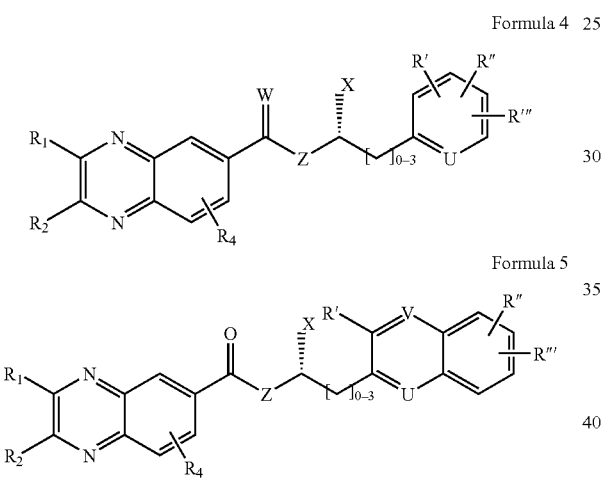

Formula 4

Formula 5 wherein U is selected from CH, CR, COR, CSR, CNHR, CNRR, $CNHCH_2COOH$, $CNHCH_2COOR$, $CNHCH_2CONH_2$, and N;

V is N, CR, or CR;

Z is NH or O;

X is COOH, COOR, $CONH_2$, CONHR, CONRR, or heterocycle;

$R_1$ and $R_2$ are independently selected from H, substituted or unsubstituted alkyl, alkenyl, alkynyl, aryl, fused aryl, heterocycle and fused heterocycle, and $R_1$ and $R_2$ together with the carbon atoms to which they are attached may form a 5- or 6-membered ring;

R', R", R''' are independently H, OH, OR, SH, SR, $NH_2$, NHR, NRR, $NO_2$, Cl, F, Br, I, CN, $N_3$, COR, COOH, COOR, $CONH_2$, CONHR, CONRR, C(=NH)NHR, $CH_2CH_2COOH$, $OCH_2COOH$, $NHCONH_2$, NHCHO, $NHSO_2R$, NHCOR, substituted or unsubstituted alkyl, alkenyl, alkynyl, aryl, fused aryl, heterocycle or fused heterocycle; and R and $R_4$ are independently H, or substituted or unsubstituted alkyl, alkenyl, alkynyl, aryl, fused aryl, heterocycle or fused heterocycle;

wherein each heterocycle is independently a 5- or 6-membered heterocyclic ring containing at least one atom of S, N, or O, and wherein substituted groups are substituted with one or more substituents selected from the group consisting of $NH_2$, OH, SH, NC, C(O)OR, aryl, alkyl, alkenyl, alkynyl, F, Cl, Br, NHCOR, $NHCONH_2$, $NHCSNH_2$, $OCH_2COOH$, $OCH_2CONH_2$, $OCH_2CONHR$, $OC(Me)_2COOH$, $OC(Me)_2CONH_2$, $NHCH_2COOH$, $NHCH_2CONH_2$, $NHSO_2R$, $NHSO_2CF_3$, $PO_3H$, $SO_3H$, $(CH_2)_{1-3}COOH$, $CH=CHCOOH$, $O(CH_2)_{1-4}COOH$, $NHCOCH_2CH(OH)COOH$, $CH(COOH)_2$, $CH(PO_3H)_2$, $OCH_2CH_2CH_2COOH$, and NHCHO.

5. A compound according to Formula 7

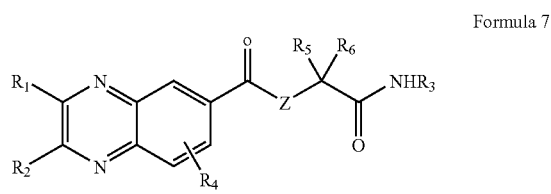

Formula 7 wherein Z is NH or O;

$R_1$ and $R_2$ are independently selected from H, substituted or unsubstituted alkyl, alkenyl, alkynyl, aryl, fused aryl, heterocycle or fused heterocycle;

$R_3$ is substituted or unsubstituted alkyl, alkenyl, alkynyl, aryl, fused aryl, heterocycle, fused heterocycle;

$R_5$ and $R_6$ are either H, alkyl, or together are connected via an additional 1–4 atoms to form a substituted or unsubstituted cyclic group containing 3–6 atoms; and wherein R and $R_4$ are H, substituted or unsubstituted alkyl, alkenyl, alkynyl, aryl, fused aryl, heterocycle or fused heterocycle;

wherein each heterocycle is independently a 5- or 6-membered heterocyclic ring containing at least one atom of S, N, or O, and wherein substituted groups are substituted with one or more substituents selected from the group consisting of $NH_2$, OH, SH, NC, C(O)OR, aryl, alkyl, alkenyl, alkynyl, F, Cl, Br, NHCOR, $NHCONH_2$, $NHCSNH_2$, $OCH_2COOH$, $OCH_2CONH_2$, $OCH_2CONHR$, $OC(Me)_2COOH$, $OC(Me)_2CONH_2$, $NHCH_2COOH$, $NHCH_2CONH_2$, $NHSO_2R$, $NHSO_2CF_3$, $PO_3H$, $SO_3H$, $(CH_2)_{1-3}COOH$, $CH=CHCOOH$, $O(CH_2)_{1-4}COOH$, $NHCOCH_2CH(OH)COOH$, $CH(COOH)_2$, $CH(PO_3H)_2$, $OCH_2CH_2CH_2COOH$, and NHCHO.

6. A pharmaceutical composition comprising a compound according to any one of claims 1–4 and 5, or a pharmaceutically acceptable salt thereof, and a pharmaceutically acceptable carrier.

7. A method of treating a hepatitis C infection, comprising administering a therapeutically effective amount of a composition according to claim 6 to a subject in need of such treatment.

* * * * *